United States Patent [19]

Fujii et al.

[11] 4,283,418
[45] Aug. 11, 1981

[54] GUANIDINOBENZOIC ACID DERIVATIVES AND PROCESS FOR THEIR PREPARATION

[75] Inventors: Setsuro Fujii, Toyonaka; Tsuyoshi Watanabe, Kadoma; Masashi Shiota, Nishinomiya; Itsuo Okumoto, Ashiya; Naohiro Kayama, Takatsuki, all of Japan

[73] Assignee: Ono Pharmaceutical Co., Ltd., Osaka, Japan

[21] Appl. No.: 123,609

[22] Filed: Feb. 22, 1980

[30] Foreign Application Priority Data

Mar. 1, 1979 [JP] Japan .................................. 54-22571
Mar. 1, 1979 [JP] Japan .................................. 54-22572

[51] Int. Cl.³ .................. A61K 31/245; C07C 101/56
[52] U.S. Cl. ................................ 424/310; 260/501.11; 260/501.12; 560/34
[58] Field of Search ......................... 560/34; 424/310; 260/501.11, 501.12

[56] References Cited

U.S. PATENT DOCUMENTS 4,021,472  5/1977  Fujii et al. .............................. 560/34

FOREIGN PATENT DOCUMENTS 1905813  3/1970  Fed. Rep. of Germany .
2846251  5/1979  Fed. Rep. of Germany .......... 424/310
47-46987  5/1972  Japan .
4987075  2/1976  Japan ....................................... 560/34

OTHER PUBLICATIONS

Fujii et al., "Chem. Absts.", 88, 50530(k), 1978.
Okamoto et al., *Keio Journal of Medicine*, 11, 105, (1962).
Kassel et al., *J. Biol. Chemistry*, 238, 3274, (1963).

*Primary Examiner*—G. T. Breitenstein
*Attorney, Agent, or Firm*—Sughrue, Rothwell, Mion, Zinn and Macpeak

[57] ABSTRACT

Guanidinobenzoic acid derivatives represented by the general formula [I]

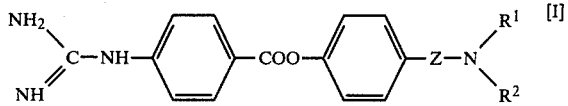

wherein $R^1$, $R^2$ and $Z$ are as defined hereinafter, having antiplasmin and anti-trypsin activities and process for their preparation as well as a pharmaceutical composition and a method of inhibiting the activity of plasmin and trypsin is disclosed.

10 Claims, No Drawings

GUANIDINOBENZOIC ACID DERIVATIVES AND PROCESS FOR THEIR PREPARATION

BACKGROUND OF THE INVENTION

1. Field of the Invention

This invention relates to novel guanidinobenzoic acid derivatives and process for their preparation.

2. Description of the Prior Art

A number of compounds are known to have anti-plasmin and anti-trypsin activities. For example, trans-4-aminomethylcyclohexanecarboxylic acid as disclosed in S. Okamoto and U. Okamoto, *Keio Journal of Medicine*, 11, 105 (1962) is known to be an anti-plasmin agent. "Trasylol" as described in B. Kassel et al, *J. Biol. Chem.*, 238, 3274 (1963) and German Patent Application (OLS) No. 1,905,813 is known to be an anti-trypsin agent, and the compounds disclosed in U.S. Pat. No. 4,021,472 are known to be both an anti-plasmin agent and an anti-trypsin agent.

However, trans-4-aminomethylcyclohexanecarboxylic acid and Trasylol have disadvantages because they exhibit relatively low activities. The compounds described in U.S. Pat. No. 4,021,472 provide the same anti-plasmin or anti-trypsin effect at a lower dosage level than can be achieved with trans-4-aminomethylcyclohexanecarboxylic acid and trasylol. However, there has been an increasing demand for compounds even more potent at a lower dosage level since reduced dosage generally means lowered side effects which is desirable from the standpoint of safety.

SUMMARY OF THE INVENTION

An object of this invention is, therefore, to provide guanidinobenzoic acid compounds which are useful as pharmaceuticals.

Another object of this invention is to provide guanidinobenzoic acid derivatives of high potency with respect to anti-plasmin or anti-trypsin pharmacological activities at low dosage levels and to provide a process for preparing such compounds.

Another object of the present invention is to provide a pharmaceutical composition having anti-plasmin and anti-trypsin activities.

A further object of the present invention is to provide a method for inhibiting the activity of plasmin and/or trypsin.

As a result of extensive research on anti-plasmin and anti-trypsin agents, it has now been found that a new series of guanidinobenzoic acid derivatives have advantagous anti-plasmin and anti-trypsin activities.

Accordingly, this invention in one embodiment provides guanidinobenzoic acid derivatives represented by the general formula [I]

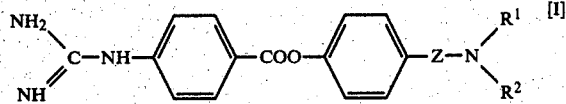

wherein Z represents a $SO_2$ group or Z'-CO group wherein Z' represents a single bond or methylene, ethylene or vinylene group, and $R^1$ and $R^2$, which may be the same or different, each represent a hydrogen atom or a lower alkyl group, and the acid addition salts of the guanidinobenzoic acid derivatives represented by the general formula [I].

In another embodiment, this invention provides a process for preparing the guanidinobenzoic acid derivatives represented by the general formula [I].

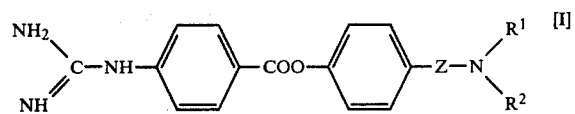

wherein the various symbols are as defined above, and the acid addition salts thereof according to claim 1, comprising reacting an acid addition salt of a compound represented by the general formula [II]

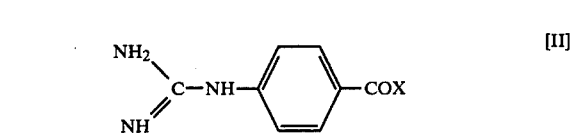

wherein X represents a halogen atom, with a compound represented by the general formula [III]

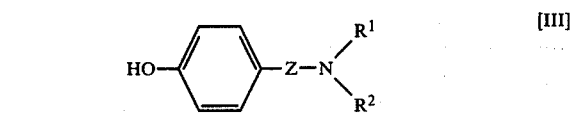

wherein the various symbols are as defined above.

DETAILED DESCRIPTION OF THE INVENTION

The term "lower alkyl" as is used throughout the specification and claims means a straight- or branched-chain alkyl group having 1 to 4 carbon atoms such as a methyl group, an ethyl group and n-propyl, isopropyl, n-butyl, sec-butyl and tert-butyl groups.

The novel guanidinobenzoic acid derivatives can be prepared according to the following reaction scheme:

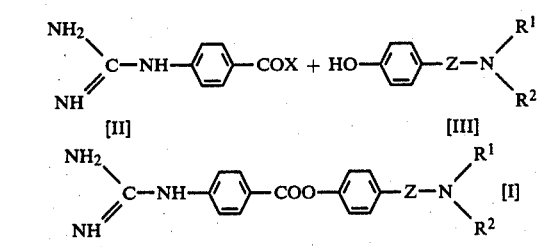

wherein the various symbols are as defined above.

The compounds of the general formula [I] can be prepared by reacting a p-guanidinobenzoyl halide represented by the general formula [II] or an acid addition salt thereof with a compound represented by the general formula [III] in an inert solvent in the presence of a dehydrohalogenating agent at a temperature ranging from $-20°$ C. to room temperature for about 1 to 5 hours.

Suitable examples of dehydrohalogenating agents, which can be used in the above reaction, include tertiary amines such as triethylamine, tri-n-butylamine, N,N-dimethylaniline, N-methylpiperidine, pyridine, etc.

Suitable examples of inert solvents, which can be used in the above reaction, include benzene, toluene, diethyl ether, tetrahydrofuran, dioxane, acetone, acetonitrile, pyridine, etc.

The inert solvents described above can be used individually or as a mixture thereof. Of these inert solvents, pyridine is most preferred since it serves both as a solvent and as a dehydrohalogenating agent.

The reaction product is produced in the form of an acid addition salt thereof. When the reaction product is obtained as crystals in the reaction mixture, it may be isolated by filtering the crystals. When the reaction product is not obtained as crystals in the reaction mixture, it may be isolated by filtering the crystals, which is precipitated by adding an aqueous solution of sodium bicarbonate to the reaction mixture or the residue obtained by concentration under reduced pressure of the reaction mixture or the solution obtained by adding a solvent which is not disolve the reaction product.

If desired, the compounds represented by the general formula [I] can further be converted into pharmaceutically acceptable acid addition salts thereof with ease according to conventional methods.

Suitable examples of acids which can be used to produce the pharmaceutically acceptable acid addition salts include inorganic acids such as hydrochloric acid, sulfuric acid, phosphoric acid, hydrobromic acid, nitric acid, etc., and organic acids such as acetic acid, lactic acid, oxalic acid, maleic acid, fumaric acid, succinic acid, tartaric acid, malic acid, citric acid, benzenesulfonic acid, toluenesulfonic acid, methanesulfonic acid, etc.

Preferred examples of pharmaceutically acceptable acid addition salts of the compound represented by the general formula [I] include methanesulfonates, toluene sulfonates, hydrochlorides, phosphates, etc.

The compounds of the general formula [II] can be prepared from p-guanidinobenzoic acid in a conventional manner.

For example, p-guanidinobenzoic acid is heated with thionyl chloride to form p-guanidinobenzoyl chloride hydrochloride, which can be used per se for further reaction in this invention.

The compounds represented by the general formula [III], wherein Z represents $SO_2$ group and the other symbols are as defined above, can be prepared in a conventional manner, for example, described Beilstein, 11, III, 506, J. Med. Chem., 8, 377 (1965), etc.

The compounds represented by the general formula [III], wherein Z represents Z'—CO group and Z', $R^1$ and $R^2$ are as defined above, can be prepared in a conventional manner, for example, by the methods described in Beilstein, 10, 164, Arzneimittel-Forsch, 14, 324 (1964) or Beilstein, 10, 191, or by reacting a ester, for example methyl, ethyl, propyl, phenyl, p-nitrophenyl or cyanomethyl ester, of the general formula:

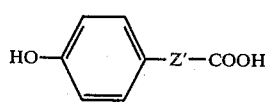

(IV)

(wherein Z' is as defined above) with a primary or secondary amine in the presence or absence of a solvent such as diethyl ether, tetrahydrofuran, methanol, ethanol, benzene, toluene, acetonitrile, etc., at a temperature ranging from room temperature to 150° C. at normal or elevated pressure. Examples of the amines are methylamine, ethylamine, n-propylamine, isopropylamine, n-butylamine, sec-butylamine, dimethylamine, diethylamine, di-n-propylamine, di-n-butylamine, diisopropylamine, N-ethyl-n-butylamine, ammonia, etc.

The compounds represented by the formula [I] and the acid addition salts thereof have potent anti-plasmin and anti-trypsin activities even at very low dosage levels.

Further, the compounds of the present invention are excellent in solubility and, therefore, are suitable for administration as a pharmaceutical in the form of an aquious solution, a physiological salt solution, liquid glucose or other solutions.

The inhibitory activities of representative compounds of the general formula [I] against plasmin and trypsin in vitro were determined in a manner similar to the method described by M. Muramatsu et al J. Biochemistry, 58, 214 (1964) for trypsin and the method described by M. Muramatsu et al ibid, 57, 402 (1965) for plasmin. The procedures used are described more specifically below.

(1) Trypsin: 0.4 ml of trypsin (1.25 μg/ml), 0.5 ml of p-tosylarginine methyl ester (20 mM) in Tris-HCl buffer (pH 8.5) and 0.1 ml of a solution of each of the following compounds represented by the general formula [I] at various concentrations was reacted at a temperature of 37° C. for 30 minutes, and the concentration of each of the test compounds at which the activity of trypsin 0.5 μg to hydrolyze p-tosylarginine methyl ester was inhibited to an extent of 50% is shown in Table 1 below.

(2) Plasmin: 0.1 ml of human euglobulin (10 fold dilution), 0.1 ml of streptokinase (2000 unit/ml), 0.4 ml of fibrinogen (4% solution), 0.3 ml of a 0.1 M borate saline buffer solution (pH 7.4) and 0.1 ml of a solution of each of the following compounds represented by the general formula [I] at various concentrations was allowed to react at a temperature of 37° C. for 30 minutes. The concentration at which the test compound exhibited inhibition against plasmin to an extent of 50% was determined, and the results obtained are shown in Table 1 below.

TABLE 1

| Compound No. | 50% Inhibition Concentration Anti-trypsin | Anti-Plasmin | Solubility in Water |
|---|---|---|---|
| 1 | $3.0 \times 10^{-9}$ M | $3.1 \times 10^{-9}$ M | >20 mM |
| 2 | $2.0 \times 10^{-9}$ M | $6.4 \times 10^{-9}$ M | >20 mM |
| 3 | $2.2 \times 10^{-9}$ M | $4.8 \times 10^{-9}$ M | >20 mM |
| 4 | $3.4 \times 10^{-9}$ M | $2.7 \times 10^{-7}$ M | >20 mM |
| 5 | $9.1 \times 10^{-9}$ M | $4.1 \times 10^{-7}$ M | >20 mM |

TABLE 1-continued

| Compound No. | 50% Inhibition Anti-trypsin | Concentration Anti-Plasmin | Solubility in Water |
|---|---|---|---|
| 6 | $1.1 \times 10^{-8}$ M | $9.5 \times 10^{-8}$ M | >20 mM |

Compound No. 1:
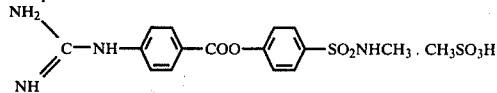

Compound No. 2:
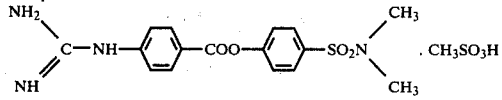

Compound No. 3:
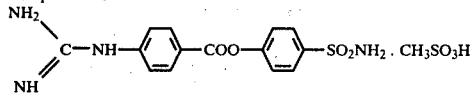

Compound No. 4:
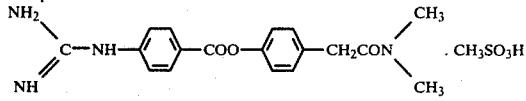

Compound No. 5:
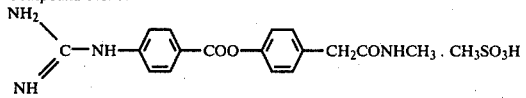

Compound No. 6:
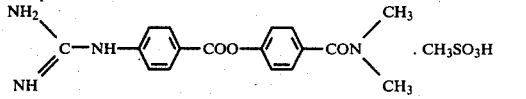

As is apparent from the above results, guanidinobenzoic acid derivatives represented by the general formula [I] and the acid addition salts thereof according to this invention are highly inhibitory to proteolytic enzymes of plasmin and trypsin and, therefore, are useful as pharmaceuticals, i.e., as an anti-trypsin agent for treating acute pancreatitis and the like or an anti-plasmin agent for treating bleeding disorders and the like.

Furthermore, it has been suggested that a protease is concerned in promotion of cancer and it is well known that a compound which inhibits a protease in vitro or in vivo, obstructs the production of cancer and, therefore, it is thought that the compounds of the present invention, which inhibit proteases such as trypsin and plasmin, are useful as anti-cancer agent.

This invention also includes in its scope pharmaceutical compositions comprising at least one of the compounds represented by the general formula [I] or pharmaceutically acceptable salts thereof and pharmaceutically acceptable carriers, diluents and excitients.

Usually the compounds or pharmaceutical compositions comprising the same are administered orally. Suitable examples of solid formulations for oral administration include tablets, pills, powders and granules. In these solid formulations one or more active ingredients are mixed with at least one inactive diluent such as calcium carbonate, potato starch, alginic acid, lactose, etc. The formulation may contain additives other than the diluents, for example, lubricants such as magnesium stearate, etc.

Suitable example of liquid formulations for oral administration include pharmaceutically acceptable emulsions, solutions, suspensions, syrups or elixirs. Conventionally used liquid diluents are, for example, water or liquid paraffin. This formulation may also contain, in addition to the diluents, auxiliary agents, for example, humectants, suspension aids, sweeteners, flavors, fragrants or antiseptics.

Capsules comprising an assimilable substance such as gelatin and which contain one or more active ingredients and a diluent or an excipient can also be used in this invention as a suitable example of formulation for oral administration.

In this invention the amount of the active ingredient in the formulation can be varied and a suitable amount determined depending on the therapeutic purpose. Dosage is determined based on the therapeutic effects desired, the number of times administered and the period of treating.

Usually, the dosage for an adult is about 100 mg to about 1 g for treating acute pancreatitis and hemorrhagic diseases by oral administration.

Preferred specific examples of guanidinobenzoic acid compounds represented by the general formula [I] of this invention include p-(p-guanidinobenzoyloxy)benzenesulfonamide,
p-(p-guanidinobenzoyloxy)-N-methylbenzenesulfonamide,
p-(p-guanidinobenzoyloxy)-N-ethylbenzenesulfonamide,
p-(p-guanidinobenzoyloxy)-N-n-propylbenzenesulfonamide,
p-(p-guanidinobenzoyloxy)-N-isopropylbenzenesulfonamide,
p-(p-guanidinobenzoyloxy)-N-n-butylbenzenesulfonamide,
p-(p-guanidinobenzoyloxy)-N-sec-butylbenzenesulfonamide,
p-(p-guanidinobenzoyloxy)-N-tert-butylbenzenesulfonamide,
p-(p-guanidinobenzoyloxy)-N,N-dimethylbenzenesulfonamide,
p-(p-guanidinobenzoyloxy)-N,N-diethylbenzenesulfonamide,
p-(p-guanidinobenzoyloxy)-N,N-di-n-propylbenzenesulfonamide,
p-(p-guanidinobenzoyloxy)-N,N-diisopropylbenzenesulfonamide,
p-(p-guanidinobenzoyloxy)-N,N-di-n-butylbenzenesulfonamide,
p-(p-guanidinobenzoyloxy)-N-methyl-N-ethylbenzenesulfonamide,
p-(p-guanidinobenzoyloxy)-N-methyl-N-n-propylbenzenesulfonamide,
p-(p-guanidinobenzoyloxy)-N-methyl-N-isopropylbenzenesulfonamide,
p-(p-guanidinobenzoyloxy)-N-methyl-N-n-butylbenzenesulfonamide,
p-(p-guanidinobenzoyloxy)-N-ethyl-N-n-propylbenzenesulfonamide,
p-(p-guanidinobenzoyloxy)-N-ethyl-N-isopropylbenzenesulfonamide,
p-(p-guanidinobenzoyloxy)-N-ethyl-N-n-butylbenzenesulfonamide,
p-(p-guanidinobenzoyloxy)-N-n-propyl-N-isopropylbenzenesulfonamide,
p-(p-guanidinobenzoyloxy)-N-n-propyl-N-n-butylbenzenesulfonamide,
p-(p-guanidinobenzoyloxy)-N-n-butyl-N-sec-butylbenzenesulfonamide,
p-(p-guanidinobenzoyloxy)benzamide,
p-(p-guanidinobenzoyloxy)-N-methylbenzamide,
p-(p-guanidinobenzoyloxy)-N-ethylbenzamide,
p-(p-guanidinobenzoyloxy)-N-n-propylbenzamide, p-(p-guanidinobenzoyloxy)-N-isopropylbenzamide,
p-(p-guanidinobenzoyloxy)-N-n-butylbenzamide,
p-(p-guanidinobenzoyloxy)-N-sec-butylbenzamide,
p-(p-guanidinobenzoyloxy)-N-tert-butylbenzamide,
p-(p-guanidinobenzoyloxy)-N,N-dimethylbenzamide,
p-(p-guanidinobenzoyloxy)-N,N-diethylbenzamide,
p-(p-guanidinobenzoyloxy)-N,N-di-n-propylbenzamide,
p-(p-guanidinobenzoyloxy)-N,N-diisopropylbenzamide,
p-(p-guanidinobenzoyloxy)-N,N-di-n-butylbenzamide,
p-(p-guanidinobenzoyloxy)-N,N-diisobutylbenzamide,
p-(p-guanidinobenzoyloxy)-N-methyl-N-ethylbenzamide,
p-(p-guanidinobenzoyloxy)-N-methyl-N-n-propylbenzamide,
p-(p-guanidinobenzoyloxy)-N-methyl-N-isopropylbenzamide,
p-(p-guanidinobenzoyloxy)-N-methyl-N-n-butylbenzamide,
p-(p-guanidinobenzoyloxy)-N-methyl-N-sec-butylbenzamide,
p-(p-guanidinobenzoyloxy)-N-ethyl-N-n-propylbenzamide,
p-(p-guanidinobenzoyloxy)-N-ethyl-N-isopropylbenzamide,
p-(p-guanidinobenzoyloxy)-N-ethyl-N-n-butylbenzamide,
p-(p-guanidinobenzoyloxy)-N-ethyl-N-sec-butylbenzamide,
p-(p-guanidinobenzoyloxy)-N-n-propyl-N-isopropylbenzamide,
p-(p-guanidinobenzoyloxy)-N-n-propyl-N-n-butylbenzamide,
p-(p-guanidinobenzoyloxy)-N-n-propyl-N-sec-butylbenzamide,
p-(p-guanidinobenzoyloxy)-N-n-butyl-N-sec-butylbenzamide,
p-(p-guanidinobenzoyloxy)phenylacetamide,
p-(p-guanidinobenzoyloxy)phenyl-N-methylacetamide,
p-(p-guanidinobenzoyloxy)phenyl-N-ethylacetamide,
p-(p-guanidinobenzoyloxy)phenyl-N-n-propylacetamide,
p-(p-guanidinobenzoyloxy)phenyl-N-isopropylacetamide,
p-(p-guanidinobenzoyloxy)phenyl-N-n-butylacetamide,
p-(p-guanidinobenzoyloxy)phenyl-N-sec-butylacetamide,
p-(p-guanidinobenzoyloxy)phenyl-N-tert-butylacetamide,
p-(p-guanidinobenzoyloxy)phenyl-N,N-dimethylacetamide,
p-(p-guanidinobenzoyloxy)phenyl-N,N-diethylacetamide,
p-(p-guanidinobenzoyloxy)phenyl-N,N-di-n-propylacetamide,
p-(p-guanidinobenzoyloy)pyenyl-N,N-diisopropylacetamide,
p-(p-guanidinobenzoyloxy)phenyl-N,N-di-n-butylacetamide,
p-(p-guanidinobenzoyloxy)phenyl-N,N-diisobutylacetamide,
p-(p-guanidinobenzoyloxy)phenyl-N-methyl-N-ethylacetamide,
p-(p-guanidinobenzoyloxy)phenyl-N-methyl-N-n-propylacetamide,
p-(p-guanidinobenzoyloxy)phenyl-N-methyl-N-isopropylacetamide,
p-(p-guanidinobenzoyloxy)phenyl-N-methyl-N-n-butylacetamide,
p-(p-guanidinobenzoyloxy)phenyl-N-methyl-N-sec-butylacetamide,
p-(p-guanidinobenzoyloxy)phenyl-N-ethyl-N-n-propylacetamide,
p-(p-guanidinobenzoyloxy)phenyl-N-ethyl-N-isopropylacetamide,
p-(p-guanidinobenzoyloxy)phenyl-N-ethyl-N-n-butylacetamide,
p-(p-guanidinobenzoyloxy)phenyl-N-ethyl-N-sec-butylacetamide,
p-(p-guanidinobenzoyloxy)phenyl-N-n-propyl-N-isopropylacetamide,
p-(p-guanidinobenzoyloxy)phenyl-N-n-propyl-N-n-butylacetamide,
p-(p-guanidinobenzoyloxy)phenyl-N-n-propyl-N-sec-butylacetamide,
p-(p-guanidinobenzoyloxy)phenyl-N-n-butyl-N-sec-butylacetamide,
p-(p-guanidinobenzoyloxy)cinnamamide,
p-(p-guanidinobenzoyloxy)-N-methylcinnamamide,
p-(p-guanidinobenzoyloxy)-N-ethylcinnamamide,
p-(p-guanidinobenzoyloxy)-N-n-propylcinnamamide,
p-(p-guanidinobenzoyloxy)-N-isopropylcinnamamide,
p-(p-guanidinobenzoyloxy)-N-n-butylcinnamamide,
p-(p-guanidinobenzoyloxy)-N-sec-butylcinnamamide,
p-(p-guanidinobenzoyloxy)-N,N-dimethylcinnamamide,
p-(p-guanidinobenzoyloxy)-N,N-diethylcinnamamide,
p-(p-guanidinobenzoyloxy)-N,N-di-n-propylcinnamamide,
p-(p-guanidinobenzoyloxy)-N,N-diisopropylcinnamamide,
p-(p-guanidinobenzoyloxy)-N,N-di-n-butylcinnamamide,
p-(p-guanidinobenzoyloxy)-N-methyl-N-ethylcinnamamide,
p-(p-guanidinobenzoyloxy)-N-methyl-N-n-propylcinnamamide,
p-(p-guanidinobenzoyloxy)-N-methyl-N-n-butylcinnamamide,
p-(p-guanidinobenzoyloxy)-N-ethyl-N-n-propylcinnamamide,
p-(p-guanidinobenzoyloxy)-N-ethyl-N-n-butylcinnamamide,
p-(p-guanidinobenzoyloxy)-N-ethyl-N-sec-butylcinnamamide,
p-(p-guanidinobenzoyloxy)-N-n-propylcinnamamide,
p-(p-guanidinobenzoyloxy)phenylpropionamide,
p-(p-guanidinobenzoyloxy)phenyl-N-methylpropionamide,
p-(p-guanidinobenzoyloxy)phenyl-N-ethylpropionamide,
p-(p-guanidinobenzoyloxy)phenyl-N-n-propylpropionamide,
p-(p-guanidinobenzoyloxy)phenyl-N-isopropylpropionamide,
p-(p-guanidinobenzoyloxy)phenyl-N-n-butylpropionamide,
p-(p-guanidinobenzyloxy)phenyl-N-sec-butylpropionamide,
p-(p-guanidinobenzoyloxy)phenyl-N,N-dimethylpropionamide,
p-(p-guanidinobenzoyloxy)phenyl-N,N-diethylpropionamide,
p-(p-guanidinobenzoyloxy)phenyl-N,N-di-n-propylpropionamide, p-(p-guanidinobenzoyloxy)phenyl-N,N-diisopropylpropionamide,
p-(p-guanidinobenzoyloxy)phenyl-N,N-di-n-butylpropionamide,
p-(p-guanidinobenzoyloxy)phenyl-N-methyl-N-ethylpropionamide,
p-(p-guanidinobenzoyloxy)phenyl-N-methyl-N-n-propylpropionamide,
p-(p-guanidinobenzoyloxy)phenyl-N-methyl-N-n-butylpropionate,
p-(p-guanidinobenzoyloxy)phenyl-N-ethyl-N-n-propylpropionamide,
p-(p-guanidinobenzoyloxy)phenyl-N-ethyl-N-n-butylpropionamide,
p-(p-guanidinobenzoyloxy)phenyl-N-n-propyl-N-n-butylpropionamide and etc.

This invention is illustrated in further detail by reference to the following Reference Example and Examples, but it should be understood that they are given for illustrative purposes only and are not to be construed as limiting the scope of the invention.

EXAMPLE 1 p-(p-Guanidinobenzoyloxy)-N,N-dimethylbenzenesulfonamide methanesulfonic acid salt 2.7 g of p-guanidinobenzoic acid was heated with 25 ml of thionylchloride at 70°–75° C. for 30 minutes with stirring. To the reaction mixture was added petroleum ether to precipitate crystals of p-guanidinobenzoyl chloride hydrochloride, which were filtered and washed with petroleum ether.

The crystals thus obtained were added to a solution of 3.0 g of N,N-dimethyl-p-hydroxybenzenesulfonamide in 20 ml of pyridine at 0° C. and the mixture was stirred for 2 hours. To the reaction mixture was added a saturated aqueous solution of sodium bicarbonate and the resulting crystals were filtered out, washed with water and acetone, and dried. The crystals thus obtained were suspended in methanol and dissolved by adding of methanesulfonic acid, the mixture was filtered and diethyl ether was added to the filtrate. The resulting crystals were filtered out, dried and recrystallized from dimethylformamide to obtain 2.75 g of the title compound.

Melting point: 211°–213° C.

| Elemental Analysis for $C_{16}H_{18}N_4O_4S \cdot CH_3SO_3H$ | | | | |
| --- | --- | --- | --- | --- |
| | C | H | N | S |
| Calculated (%): | 41.91 | 3.96 | 12.22 | 13.98 |
| Found (%): | 42.22 | 3.74 | 12.47 | 14.19 |

EXAMPLE 2 p-(p-Guanidinobenzoyloxy)-N-methylbenzenesulfonamide methanesulfonic acid salt 4.48 g of p-guanidinobenzoic acid was converted into p-guanidinobenzoyl chloride hydrochloride in the same manner as described in Example 1.

The crystals thus obtained were added to a solution of 4.68 g of N-methyl-p-hydroxybenzenesulfonamide in 32 ml of pyridine at 0° C. and the mixture was stirred for 2 hours.

The post-treatments and recrystallization were carried out in the same manner as described in Example 1 to obtain 3.89 g of the title compound.

| Elemental Analysis for $C_{15}H_{16}N_4O_4S \cdot CH_3SO_3H$ | | | | |
| --- | --- | --- | --- | --- |
| | C | H | N | S |
| Calculated (%): | 40.53 | 3.63 | 12.61 | 14.43 |
| Found (%): | 40.71 | 3.90 | 12.44 | 14.65 |

EXAMPLE 3 p-(p-Guanidinobenzoyloxy)benzenesulfonamide methanesulfonic acid salt 3.58 g of p-guanidinobenzoic acid was converted into p-guanidinobenzoyl chloride hydrochloride in the same manner as described in Example 1.

The crystals thus obtained were added to a solution of 3.46 g of p-hydroxybenzenesulfonamide in 26 ml of pyridine at room temperature and the mixture was stirred for 2 hours.

The post-treatments and recrystallization were carried out in the same manner as described in Example 1 to obtain 3.87 g of the title compound.

Melting point: over 225° C.

| Elemental Analysis for $C_{14}H_{14}N_4O_4S \cdot CH_3SO_3H$ | | | | |
| --- | --- | --- | --- | --- |
| | C | H | N | S |
| Calculated (%): | 39.06 | 3.28 | 13.02 | 14.90 |
| Found (%): | 39.23 | 3.06 | 13.15 | 14.81 |

REFERENCE EXAMPLE 1

N-Methyl-p-hydroxyphenylacetamide

To a solution of 7.6 g of p-hydroxyphenylacetic acid in 100 ml of acetonitrile were added 8.4 g of p-nitrophenol and 10.3 g of dicyclohexylcarbodiimide at room temperature with stirring, and the resulting crystals of dicyclohexylurea were filtered out. An ethereal solution of 7.8 g of methylamine was added to the filtrate containing p-nitrophenyl p-hydroxyphenylacetate, the mixture was allowed to stand to precipitate crystals. The crystals obtained were filtered out and washed with diethyl ether to obtain 4.0 g of the title compound.

Melting point: 150°–152° C.

EXAMPLE 4 p-(p-Guanidinobenzoyloxy)phenyl-N,N-dimethylacetamide methanesulfonic acid salt 5.37 g of p-guanidinobenzoic acid was converted into p-guanidinobenzoyl chloride hydrochloride in the same manner as described in Example 1.

The crystals thus obtained were added to a solution of 5.37 g of N,N-dimethyl-p-hydroxyphenylacetamide, which was prepared by the same procedure as described in Reference Example 1, in 20 ml of pyridine at 0° C. and the mixture was stirred for 2 hours. To the reaction mixture was added 100 ml of diethyl ether and the supernatant solution was separated by decantation. To the resulting crystals were filtered out, washed with water and acetone, and dried. The crystals thus obtained were suspended in methanol and dissolved by adding of methanesulfonic acid (pH 3), and the mixture was filtered and diethyl ether was added to the filtrate. The resulting crystals were filtered out and recrystallized from methanol to obtain 7.71 g of the title compound.

Melting point: 204°–207° C.

| Elemental Analysis for $C_{18}H_{20}N_4O_3 \cdot CH_3SO_3H$ | | | | |
|---|---|---|---|---|
| | C | H | N | S |
| Calculated (%): | 49.53 | 4.96 | 12.84 | 7.35 |
| Found (%): | 49.71 | 4.43 | 12.98 | 7.13 |

EXAMPLE 5 p-(p-Guanidinobenzoyloxy)phenyl-N-methylacetamide methanesulfonic acid salt 7.16 g of p-guanidinobenzoic acid was converted into p-guanidinobenzoyl chloride hydrochloride in the same manner as described in Example 1.

The crystals thus obtained were added to a solution of 6.93 g of N-methyl-p-hydroxyphenylacetamide (prepared as described in Reference Example 1) in 26 ml of pyridine at 5° C. and the mixture was stirred for 2 hours.

The post-treatments and recrystallization were carried out in the same manner as described in Example 4 to obtain 8.92 g of the title compound.

Melting point: 166°–168° C.

| Elemental Analysis for $C_{17}H_{18}N_4O_3 \cdot CH_3SO_3H$ | | | | |
|---|---|---|---|---|
| | C | H | N | S |
| Calculated (%): | 48.33 | 4.29 | 13.27 | 7.59 |
| Found (%): | 48.57 | 4.42 | 13.03 | 7.45 |

EXAMPLE 6 p-(p-Guanidinobenzoyloxy)-N,N-dimethylbenzamide methanesulfonic acid salt 4.48 g of p-guanidinobenzoic acid was converted into p-guanidinobenzoyl chloride hydrochloride in the same manner as described in Example 1.

The crystals thus obtained were added to a solution of 4.95 g of N,N-dimethyl-p-hydroxybenzamide in 17 ml of pyridine at 0° C. and the mixture was stirred at 5° to 10° C. for 2 hours.

The post-treatments were carried out in the same manner as described in Example 4 and the crystals thus obtained were recrystallized from dimethylformamide to obtain 5.31 g of the title compound.

Melting point: 180°–181° C.

| Elemental Analysis for $C_{17}H_{18}N_4O_3 \cdot CH_3SO_3H$ | | | | |
|---|---|---|---|---|
| | C | H | N | S |
| Calculated (%): | 48.33 | 4.29 | 13.27 | 7.59 |
| Found (%): | 48.65 | 4.03 | 13.44 | 7.73 |

What is claimed is:

1. Guanidinobenzoic acid derivatives represented by the formula [I]

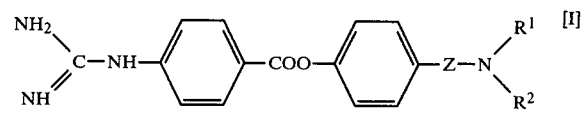

wherein Z represents a $SO_2$ group or Z'—CO group wherein Z' represents a single bond or a methylene, ethylene or vinylene group, and $R^1$ and $R^2$, which may be the same or different, each represent a hydrogen atom or a lower alkyl group, and the acid addition salts thereof.

2. A compound according to claim 1 which is p-(p-guanidinobenzoyloxy)-N,N-dimethylbenzenesulfonamide.

3. A compound according to claim 1 which is p-(p-guanidinobenzoyloxy)-N-methylbenzenesulfonamide.

4. A compound according to claim 1 which is p-(p-guanidinobenzoyloxy)benzenesulfonamide.

5. A compound according to claim 1 which is p-(p-guanidinobenzoyloxy)phenyl-N,N-dimethylacetamide.

6. A compound according to claim 1 which is p-(p-guanidinobenzoyloxy)phenyl-N-methylacetamide.

7. A compound according to claim 1 which is p-(p-guanidinobenzoyloxy)-N,N-dimethylbenzamide.

8. A compound as claimed in any preceding claim, wherein said acid addition salt is a salt of hydrochloric acid, sulfuric acid, phosphoric acid, hydrobromic acid, nitric acid, acetic acid, lactic acid, oxalic acid, maleic acid, fumaric acid, succinic acid, tartaric acid, malic acid, citric acid, benzenesulfonic acid, toluenesulfonic acid or methanesulfonic acid.

9. A pharmaceutical composition having anti-plasmin and anti-trypsin activity comprising a therapeutically effective amount of at least one guanidinobenzoic acid derivative represented by the formula (I) or an acid addition salt thereof as claimed in claim 8 and one or more pharmaceutically acceptable carriers or diluents.

10. A pharmaceutical composition having anti-plasmin and anti-trypsin activity comprising a therapeutically effective amount of at least one guanidinobenzoic acid derivative represented by the formula (I) or an acid addition salt thereof as claimed in any one of claims 1 to 7 and one or more pharmaceutically acceptable carriers or diluents.